United States Patent [19]
Daniels

[11] 4,067,565
[45] Jan. 10, 1978

[54] PREMATURE INFANT IMMOBILIZER AND HOLDING ASSEMBLY FOR THE NURSERY AND RADIOLOGICAL EXPOSURE

[76] Inventor: John E. Daniels, 3765 Herman, San Diego, Calif. 92104

[21] Appl. No.: 781,628

[22] Filed: Mar. 28, 1977

[51] Int. Cl.² .............................................. A61G 13/00
[52] U.S. Cl. ..................................................... 269/328
[58] Field of Search .......................... 269/328; 128/134; 250/439, 444, 451, 456

[56] References Cited

U.S. PATENT DOCUMENTS

| | | | |
|---|---|---|---|
| 3,215,834 | 11/1965 | Tayman | 269/328 |
| 3,358,141 | 12/1967 | Hoffmann et al. | 269/328 |
| 3,873,841 | 3/1975 | Cabansag | 269/328 |
| 4,027,869 | 6/1977 | Rviz | 269/328 |

Primary Examiner—Robert C. Watson
Attorney, Agent, or Firm—Frank D. Gilliam

[57] ABSTRACT

A premature infant immobilizer and holding assembly for the nursery and radiological exposure. The assembly comprises an x-ray pervious body platform, x-ray pervious restraining straps formed of small side-by-side pillows at least partially filled with a fluid, gas, fine powder, rolls of plastic foam or the like. The body platform includes a recess beneath the position of the infant for the placement of x-ray film. A support bracket is provided with a flat base for resting on a supporting surface and has "U" shaped channel along one edge thereof for supporting the film when x-rays of the infant are taken laterally either left or right and for supporting both the x-ray film and x-ray pervious body portion when x-rays are taken with the infant in either the decubitus or Trendelenberg positions. A rectangular body support is included when the infant is in the decubitus position and an angular body support is included when the infant is in the Trendelenberg position. An additional flat strap is provided to aid in support of the infants legs in either the decubitus or Trendelenberg positions.

15 Claims, 9 Drawing Figures

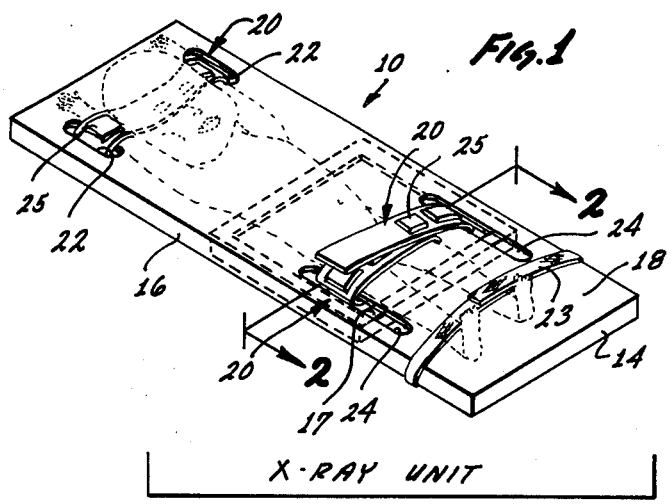
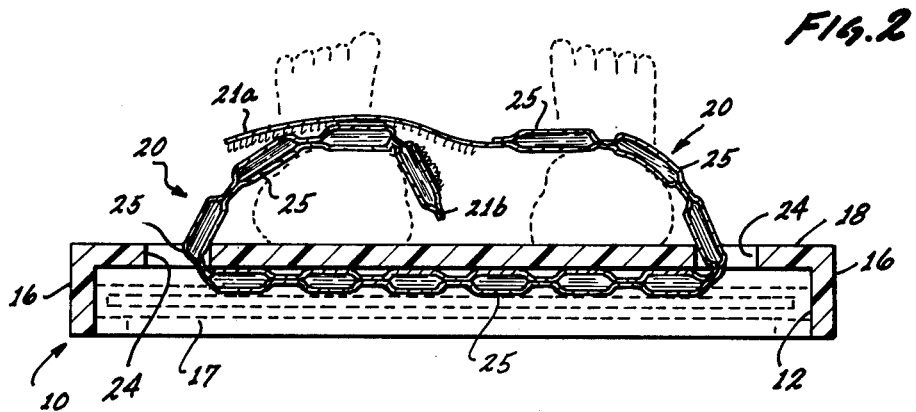
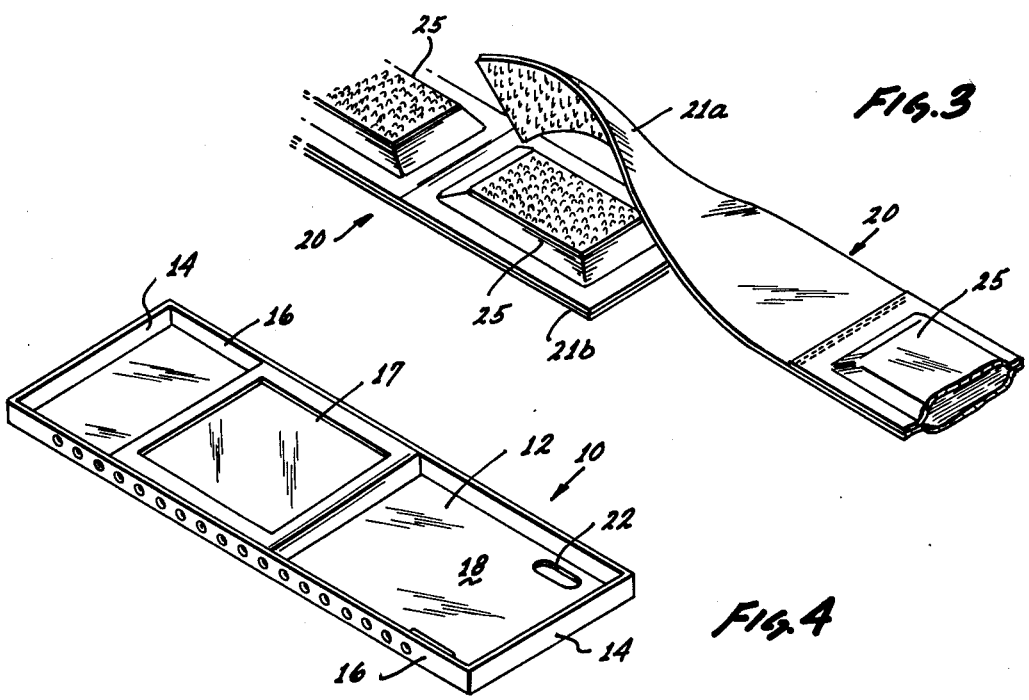

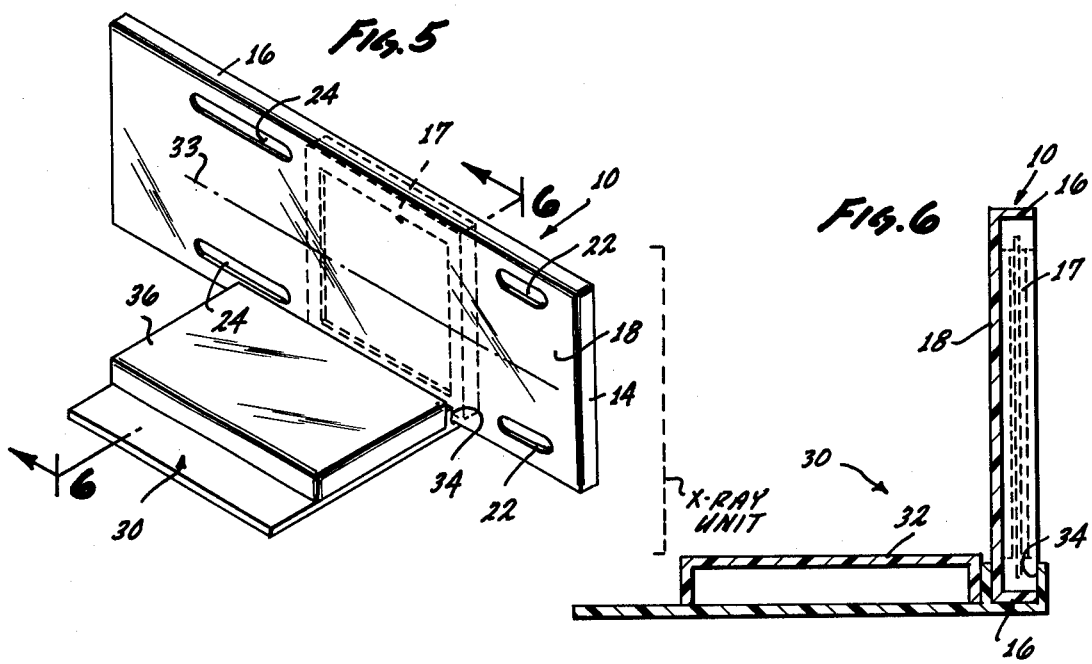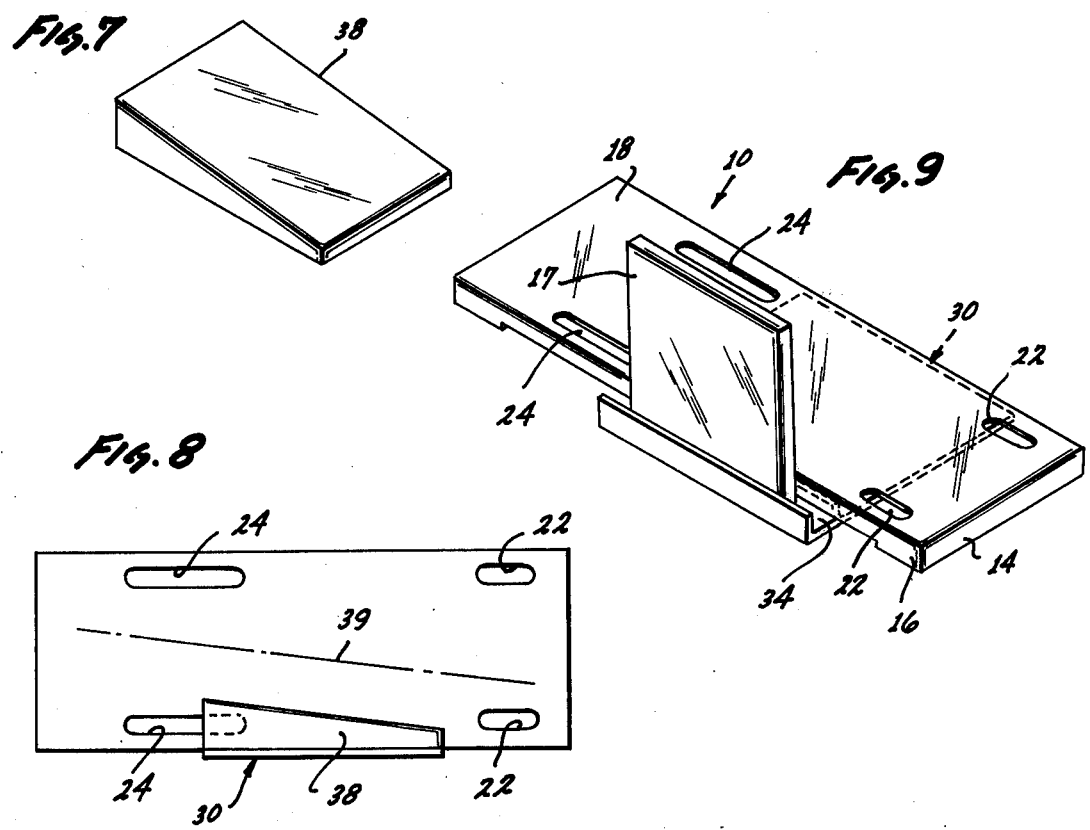

PREMATURE INFANT IMMOBILIZER AND HOLDING ASSEMBLY FOR THE NURSERY AND RADIOLOGICAL EXPOSURE

BACKGROUND OF THE INVENTION

This invention relates to a device for the immobilizing of a premature infant while employing life support systems and/or radiographic diagnostic procedures while confined to bassinets, incubators, isolettes or merely for positioning on x-ray tables or the like. The apparatus of the instant invention is specifically directed to provide a restraint to premature infants undergoing diagnostic or fluoroscopy radiological examinations during their periods of intensive care treatment without disturbing any life support systems in use by the infant, such as, for example, oxygen connections, intervenous connections, body drainage systems including chest tubes and catheters.

The present state of the art includes various restraining devices as taught by U.S. Pat. Nos. 3,892,399, 3,215,834, and 3,040,174.

In general, these prior art patents teach devices that are not designed to handle the premature infant of small size with weight from 1 to 8 pounds. These prior art devices do not teach the restraining of premature infants within bassinets, incubators or isolettes while attached to the various life support systems. Nor do they teach supporting the infant in the decubitus or Trendelenberg position during radiographic diagnostic procedures without being held by medical personnel which are also placed in line with the x-ray beam. Both federal and state laws require a minimum of x-ray exposure by medical personnel and only in extreme emergency and then only when strict safety precautions are complied with.

The device taught by U.S. Pat. No. 3,892,399 is basically a means for restraining a normal size baby in a seated position. The device taught by U.S. Pat. No. 3,215,834 is somewhat similar to the instant invention only in the respect that for certain x-ray pictures, the film is positioned below the baby. There are no teachings for positioning the baby in either the decubitus or Trendelenberg positions or the necessity of placing the x-ray film closely adjacent the baby to provide for maximum definition, the film to insure that details of the small features of a premature infant can be maximized. The device taught by U.S. Pat. No. 3,040,171 teaches generally the same concepts of the aforementioned U.S. Pat. No. 3,215,834 and includes the same deficiencies.

There has not been an entirely successful restaining device for a premature infant until the emergence of the instant invention.

SUMMARY OF THE INVENTION

Generally stated, in the presently preferred embodiment, the restraining apparatus of the instant invention comprises an x-ray pervious body platform to which the premature infant is secured by a pair of straps around the arm and head and the thighs made from a plurality of side-by-side soft hollow pillow members at least partially filled with an easily deformable material, such as, but not limited to, a liquid, foam plastic rolls, fine powder, gas or the like to provide a soft cushion contact with the fragile infant that conforms to the features of the infant, thereby, preventing any injury to infant while restrained. The body platform has a recessed area beneath the upper surface supporting the infant of substantially the same height as the film when in a cassette or other holding means so that the film itself is positioned closely adjacent the body of the infant so as to decrease distortion and increase the definitions of the anatomical parts shown on the radiographic film when exposed. A support bracket is provided to hold either the film and the body support platform for exposure of the infant in the decubitus or Trendelenberg positions or the film alone for exposure of the infant in either right or left lateral position. The base portion of the support bracket rests on any level surface. Infant body supports are provided for supporting the weight of the infant when in either the decubitus or Trendelenberg positions.

It is an object of this invention to provide an apparatus which will completely and safely immobilize a premature infant while the infant is placed in various positions.

Another object of this invention is to provide a means for radiological or fluoroscopy exposure of premature infants without exposure to medical personnel.

Another object of this invention is to provide a means for insuring the placement of the x-ray film in close proximity to the body of the infant.

Another object of this invention is to provide an immobilization apparatus for a premature infant that can be placed in conventional bassinets, incubators, and isoletts as well as x-ray tables.

Still another object of this invention is to provide an immobilizing apparatus for a premature infant that includes restraining straps that are soft, flexible and easily conform to the body features of the infant.

Still another object of the invention is to provide an apparatus as described that is portable, light in weight, strong an inexpensive to manufacture.

BRIEF DESCRIPTION OF THE DRAWINGS

FIG. 1 is a perspective showing of the infant support platform with the infant secured thereon in an immobilized position and showing one position of the film.

FIG. 2 is an end view of FIG. 1 taken along lines 2—2 showing one of the main infant restraining straps, infant support platform and the film.

FIG. 3 is partial cutaway showing of the construction of the main restraining straps and their end securing means.

FIG. 4 is a perspective view of the bottom of the infant support platform showing the film and locating apertures positioned along one side thereof.

FIG. 5 is a perspective view of the infant support platform and film held by the "U" channel perpendicular to the support bracket base including a rectangular infant body support.

FIG. 6 is an end view taken along lines 6—6 of FIG. 5.

FIG. 7 is an angular infant body support member.

FIG. 8 is a front view of FIG. 5 with the angular infant body support member in position.

FIG. 9 is a perspective showing of the infant body support member resting on the supporting surface of the support bracket with one edge positioned adjacent the film within the "U" bracket.

DESCRIPTION OF THE PREFERRED EMBODIMENT

The immobilizer of the instant invention generally comprises a flat, relatively stiff or rigid x-ray pervious infant support platform, which may be constructed of any material suitable for the purpose intended, such as, but not limited to plastic or the like adopted to support and have secured thereto in supine position a premature infant subject to be restrained in its bassinete, isolette, incubator or the like or an infant who is to be exposed to radiographic diagnostic procedures or both. In addition to the infant support platform, a support bracket is provided that includes a base portion for resting on a flat surface. The base portion has a "U" channel positioned and secured along one of its outer edges for supporting the infant support platform with the infant secured thereto and the x-ray film or the film alone with the infant support platform resting horizontal on the base portion.

In the various figures, the infant platform 10 is of a generally rectangular form having a length and width sufficient to extend in all directions beyond the dimensions of the infant and be small enough to fit into conventional bassinets, isolettes, incubators and the like. The platform 10 has a recessed portion 12 defined by the end and side walls 14, 16 respecfully. The recessed portion 12 has a depth and width substantially equal in size to a film holder or film cassette 17 (throughout this disclosure, the term film cassette will denote any type of conventional or non-conventional x-ray film and its holder means), so that the exposable surface of the x-ray film is positioned relatively close to the surface 18 supporting the infant as possible so that the film cassette 17 is positioned as near to the body of the infant as practical. It should be understood that premature infants for which this apparatus is designed have extremely small body portions so that the closer the film to the portion of the body being x-rayed, the better the quality of the resulting x-ray.

As can be seen in FIG. 1, the infant is secured to the infant support platform 10 by means of two restraining straps 20 that pass beneath the support platform through openings 22, 24 in the surface 18 of the body platform 10 and have ends 21a, 21b that fasten together to secure the infant to the body platform 10. The openings 22 are positioned at the head of the infant and have substantially the same dimensions as the width and thickness of the strap 20. This allows for the strap at the head of the infant to be fixed in position with respect to the body platform. The openings 24 are located on the opposite end of the body platform near the legs of the infant. The openings 24 are longitudinally elongated to allow adjustment of the position of the strap near the legs of the infant longitudinally to adjust for various infant lengths. The strap near the head passes over the infants arms and behind the head where the ends 21a and 21b may be fastened together. The opposite strap is positioned in openings 24 so that the strap will pass over and fasten in the thigh area of the infant. The two straps 20 are sufficient to secure the infant safely to the body platform. An additional strap 23, see FIG. 1, may be required to hold the legs of the infant in place on the body platform when the infant is positioned in decubitus or Trendelenberg positions. These straps are constructed of any suitable soft, pliable material, such as, but not limited to, plastic, rubber, natural or synthetic cloth or the like. The only limitation being that they must be impervious to filler material required by the head and thigh straps 20, hereinafter discussed in detail, and be pervious to x-rays.

Referring now to FIGS. 2 and 3, the straps 20 are formed by a plurality of side-by-side connected pillows 25 having sealable compartments. The sealable compartmetns are partially filled with liquid, gas, fine powder, foam plastic, foam rubber or the like pervious to x-rays. The material of the pillows is required to be readily formable in a manner so as to conform to the features of the infant where they contact in a manner that firmly secures the infant to the support platform and yet be safe to the infant. As can be seen in FIG. 3, the ends 21a and 21b of the straps 20 as well as the ends of strap 23 are provided with a trademarked fastening material known as Velcro. The material has either hooks or eyes on one outer surface and are held together when joined. Although Velcro is the preferred fastening means, any other outer fasteners suitable for the purpose described may be utilized to practice the invention.

Referring now to FIG. 4, along one side wall 16 of the infant support platform 10 is a row of apertures 28. These apertures allow the x-ray technecian to properly position the film cassette 17 with respect to that portion of the infants body described to be x-rayed when the material of construction of the infant support platform 10 is not transparent to the eye although x-ray pervious.

Referring now to FIGS. 5 and 6, a holding member 30 is shown. This holding member 30 has a flat base portion 32 for resting on the bottom surface of the bassinet, incubator, isolette, x-ray table or the like for supporting the body platform and infant. Along one side of the base portion 32 is a "U" channel 34. As shown in FIG. 5, the "U" channel 34 (partially hidden) is supporting both the infant support platform 10 and the film cassette 17, the film cassette being positioned within the recessed portion 12 of the infant support platform 10 (shown in phantom). An infant body support member 36 is shown positioned upon the base 30. This infant body support member supports the infant's body substantially parallel with the base portion 32 when the infant is positioned in the decubitus position along the center line 33 of FIG. 5. FIG. 6 shows a cutaway side view of the various components of FIG. 5.

FIG. 7 shows an infant body support member 38 having a generally triangular cross-section. This infant body support member 38 like the aforementioned infant body support member 36 is utilized for supporting and sloping the center line of the infant in the Trendelenberg position along line 39 as shown in FIG. 8.

FIG. 9 shows the infant support platform 10 resting on the base portion 32 of the holding member 30 and the film cassette 17 is positioned in and held by the "U" channel 34. Lateral x-rays of the infant are taken in this position. In order to snuggly secure the film cassette in the "U" channel 34 when required, the side wall 16 of the infant support platform is placed within the "U" channel 34 between one wall of the channel and the film cassette 17. In order to maintain a level infant support platform 10, when required, a portion of a side wall 16 may be partially removed as shown. The removed portion would be substantially the same thickness as the floor 18 of the infant support platform 10.

It should be easily understood that if the premature infant is secured to the infant support platform prior to being placed in its bassinet, incubator, isollette or the like, where life support systems are likely to be attached, the infant can be restrained and yet be ready at anytime if it is determined that x-rays are required, the infant need not be removed from his temperature controlled environment nor do the life support systems need to be affected.

From the foregoing detailed discussion, it will be evident that there are a number of changes, adaptations and modifications of the present invention which comes within the province of those skilled in the art. However, it is intended that all such variations not departing from the spirit of the invention, be considered as within the scope thereof and limited solely by the appended claims.

Having thus described the invention, what is claimed as new and useful and desired to be secured by U.S. Letters Patent is:

1. A premature infant immobilizer and holding assembly for a nursery and radiological exposure comprising:
   an x-ray pervious body platform with downward extending walls forming a recess for receiving x-ray film therein, said recess being substantially the same height as said x-ray film;
   x-ray pervious restraining straps secured to said body platform and having fastening means for securing said infant to said body platform, said straps being of sufficient width and flexibility to prevent injury to said infant while secured thereby; and
   a base member for supporting said body platform and said x-ray film;
   said base member comprises a flat portion and a channel member, said flat portion for supporting said body platform in a first position and said x-ray film in a first position and said channel member for supporting said body platform in a second position and said x-ray film in a second position.

2. The invention as defined in claim 1, wherein said channel member is positioned along one edge of said body platform.

3. The invention as defined in claim 1, wherein said body platform has two opposed pair of longitudinal apertures through the infant supporting surface and said restraining straps pass through said longitudinal apertures.

4. The invention as defined in claim 1, additionally comprises a rectangular body support member for supporting said infant when said body platform is in said second position.

5. The invention as defined in claim 1, additionally comprising a wedge shaped body support member for supporting said infant when said body platform is in said second position.

6. The invention as defined in claim 3, wherein at least one pair of said longitudinal apertures is substantially longer than the width of said restraining straps for longitudinal positioning of said straps according to the length of said infant.

7. The invention as defined in claim 1, wherein said fastening means comprises Velcro.

8. The invention as defined in claim 1, wherein said body platform is provided with location means for locating said film cassette with respect to a desired portion of said infant.

9. The invention defined in claim 8, wherein said location means comprises a plurality of apertures positioned along at least one wall of said body platform.

10. The invention as defined in claim 3, wherein an additional strap is provided for restraining the legs of the infant when positioned in the decubitus and Trendelenberg positions.

11. A premature infant immobilizer and holding assembly for a nursery and radiological exposure comprising:
    an x-ray pervious body platform with downward extending walls forming a recess for receiving x-ray film therein, said recess being substantially the same height as said x-ray film;
    x-ray pervious restraining straps secured to said body platform and having fastening means for securing said infant to said body, said straps being of sufficient width and flexibility to prevent injury to said infant while being secured thereby; and
    a base member for supporting said body platform and said x-ray film;
    said restraining straps are constructed of a plurality of separate sealed partially filled hollow pillows.

12. The invention as defined in claim 11, wherein said pillows are partially filled with a fluid.

13. The invention as defined in claim 11, wherein said hollow pillows are partially filled with a gas.

14. The invention as defined in claim 11, wherein said pillows are partially filled with a fine powder.

15. The invention as defined in claim 11, wherein said hollow pillows are partially filled with a soft pliable material.

* * * * *